US00PP11399P

United States Patent [19]

Verwer

[11] Patent Number: Plant 11,399

[45] Date of Patent: Jun. 6, 2000

[54] DAHLIA PLANT NAMED 'KARMA AMANDA'

[75] Inventor: Aad Verwer, Lisse, Netherlands

[73] Assignee: Fa. Gebr. Verwer, Lisse, Netherlands

[21] Appl. No.: 09/026,007

[22] Filed: Feb. 19, 1998

[30] Foreign Application Priority Data

Apr. 7, 1997 [NL] Netherlands ..... DHL 74

[51] Int. Cl.[7] ..... A01H 5/00

[52] U.S. Cl. ..... Plt./321

[58] Field of Search ..... Plt./321

[56] References Cited

PUBLICATIONS

GTITM UPOVROM Citation For 'Karma Amanda' As Per NL PBR DHL0074; Apr. 7, 1997.

*Primary Examiner*—Howard J. Locker
*Assistant Examiner*—Kent L. Bell
*Attorney, Agent, or Firm*—Christie, Parker & Hale, LLP

[57] ABSTRACT

A dahlia plant variety producing bicolor flowers comprising a creamy white base and violet apex with strong violet streaking all the way to base, violet streaking becomes gradually lighter towards base.

1 Drawing Sheet

BACKGROUND OF THE INVENTION

The present invention relates to a new and distinct variety of *dahlia hybrida* known by the varietal denomination 'Karma Amanda'. The seed parent is an unnamed seedling cross of 'Stratos' and 'Oriental Dream', both of which are unpatented, undistributed varieties. The pollen parent is unknown due to open pollination.

SUMMARY OF THE INVENTION

The new variety is a dahlia plant useful for growing outdoors and under glass which produces attractive creamy white and violet bicolor flowers. Among the traits possessed by the new variety which in combination distinguish it from other varieties known to the inventor are its attractive flowers borne on long stems.

Asexual reproduction by cuttings of the new variety in The Netherlands has demonstrated that the combination of characteristics as described herein for 'Karma Amanda' are firmly fixed and are retained through successive generations of asexual reproduction.

COMPARISON WITH PARENT

The new variety differs from its parent in flower color.

BRIEF DESCRIPTION OF ILLUSTRATION

The accompanying color photographic illustration shows a typical bloom and leaves of the new variety in colors as nearly true as possible with an illustration of this type.

DESCRIPTION OF THE NEW VARIETY

In the following description, color references are to The Royal Horticultural Society Colour Chart, where color values refer to color plate numbers in this chart.

The following observations are of plants described and grown in The Netherlands under outdoor conditions which approximate those generally used in commercial practice.

'Karma Amanda' has not been observed under all possible environmental conditions. The phenotype may vary with variations in environment such as temperature, light intensity, day length and cultural conditions.

Plant:

*Form.*—Upright, spreading.
*Height.*—About 90 cm.
*Branching characteristics.*—Moderately branching.
*Hardiness.*—Plants are winter hardy to 0° C.
*Flowering season.*—July to November in The Netherlands under glass.
*Disease resistance.*—Similar to the species.
*Flower stem.*—Length: About 60 cm. Color: Near 146D.
*Foliage.*—Single and compound. Quantity: Many. Size of leaf: Length: Single about 5 cm., compound about 20 to 25 cm. Shape of leaf: apex acute, base rounded. Leaf edge: Dentate. Texture: Leaf upperside: Leathery. Leaf under side: Smooth. Color: Leaf upperside: Near 137A. Leaf under side: Near 148B Venation: Pinnate. Petiole lenth: Terminal, longest petioles are about 10 cm; lateral, petioles are about 5 cm. Stipules: None. Stem color: Near 151A.

Bud:

*Form.*—Globular.
*Size.*—About 1 cm.
*Opening rate.*—About 20 days.
*Color of ray florets.*—When sepals first divide near 84B; when ray florets begin to unfurl near 84A.

Flower:

*Inflorescence form.*—Blooms borne singly.
*Bloom form.*—Decorative.
*Bloom diameter.*—About 14 cm.
*Typical number of blooms harvested per plant per season.*—About 20–30.
*Flowering.*—2 to 3 branches are produced with flowers occurring about 30 to 35 days later; apex of each ray floret is violet.
*Color tonality from a distance.*—Creamy white and violet.
*Lasting quality.*—About 15 to 20 days on plant; 10 to 12 days after cutting.

Ray florets:

*Length.*—About 6.1 cm.
*Width.*—About 2.4 cm.
*Shape.*—Oblong.
*Apex.*—Obtuse.
*Base.*—Rounded.

*Color.*—Bicolor; base creamy white, apex violet with strong violet streaking all the way to base, violet streaking becomes gradually lighter towards base Inner ray florets (upper surface and undersurface) Near 155B, top near 84A Outer ray florets (upper surface and undersurface) Near 155B; stripes of violet near 84B, stripes become solid at approximately top ⅓ of ray floret. Point of ray floret attachment: Near 155B. As bloom ages: Fading more to white. Fragrance: None.

Disc florets:

*Number.*—About 20.

*Length.*—About 1.3 cm.

*Color.*—Near 7A.

*Shape.*—Cylindric.

Reproductive organs:

*Stamens.*—Tubular, near 17A.

*Anthers.*—About 2 mm; color near 17B.

*Pollen.*—Near 16A.

*Pistils.*—Styles length about 1.5 mm, color near 1D; stigmas divided, near 12A.

*Character of ovaries.*—1 per pistil.

I claim:

1. A new and distinct dahlia plant of the variety substantially as shown and described.

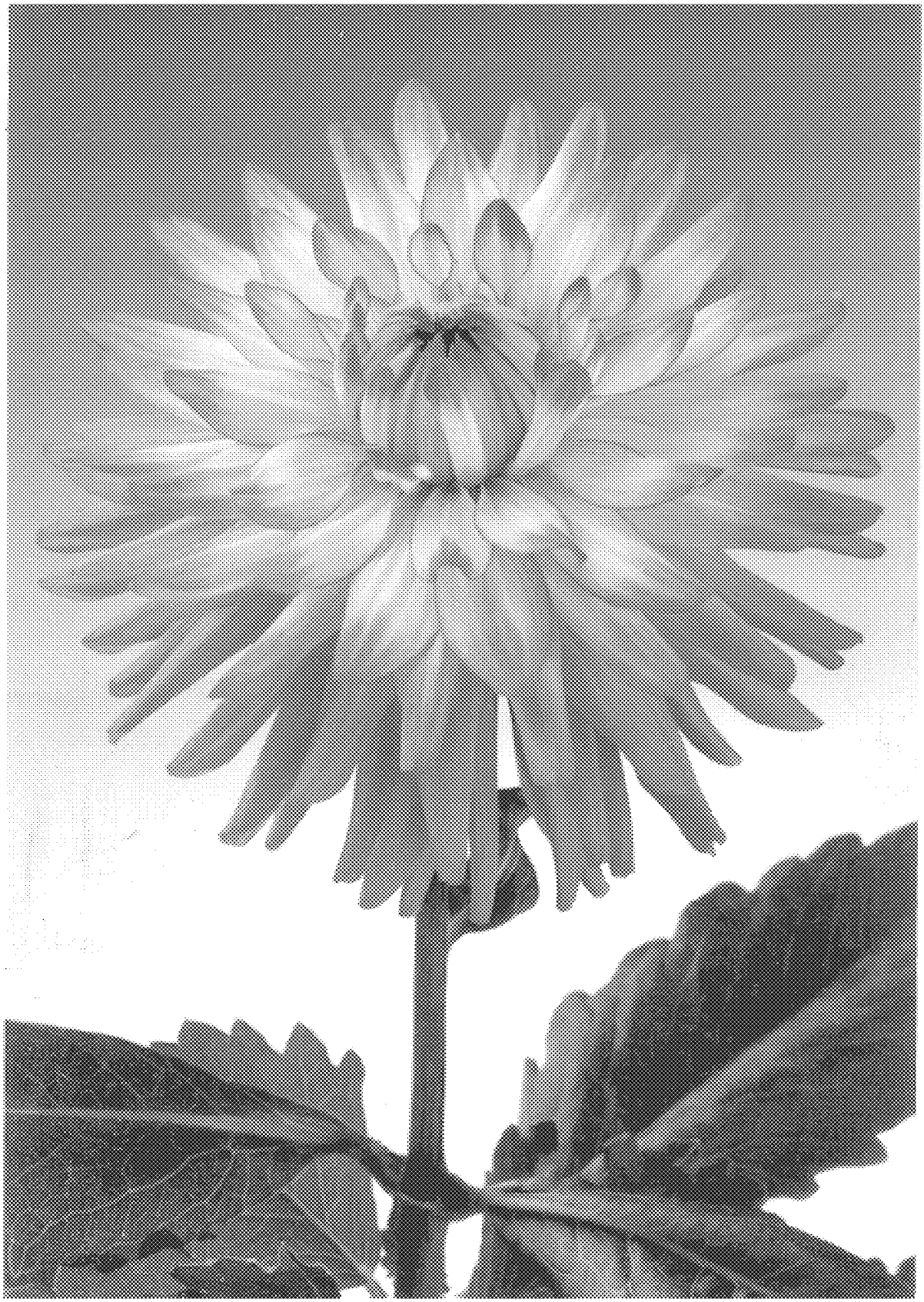

* * * * *